United States Patent [19]
Sheldon et al.

[11] Patent Number: 5,536,874
[45] Date of Patent: Jul. 16, 1996

[54] PROCESS FOR PREPARING ARYLACETIC ACID AND ARYLPROPIONIC ACID DERIVATIVES

[75] Inventors: Roger A. Sheldon, Rijswijk; Leendert Maat, Vlaardingen; Georgios Papadogianakis, Delft, all of Netherlands

[73] Assignee: Hoechst Celanese Corporation, Sommerville, N.J.

[21] Appl. No.: 347,027

[22] Filed: Nov. 30, 1994

[51] Int. Cl.$^6$ .................................................. C07C 51/10
[52] U.S. Cl. ........................... 562/406; 558/353; 560/10; 560/11; 560/12; 560/20; 560/21; 560/19; 560/37; 560/48; 560/51; 560/55; 560/56; 560/75; 560/80; 560/81; 560/100; 560/102; 560/105; 560/8
[58] Field of Search .................. 562/406; 560/100, 560/102, 105, 8

[56] References Cited

U.S. PATENT DOCUMENTS 4,981,995  1/1991  Elango ...................................... 562/406
5,166,418  11/1992  Hendricks ................................ 562/406

*Primary Examiner*—Michael L. Shippen
*Attorney, Agent, or Firm*—James J. Mullen; Donald R. Cassady

[57] ABSTRACT

There is provided a process for preparing an arylacetic acid or arylpropionic acid divative from an arylcarbinol which comprises the step of subjecting said arylcarbinol to suitable carbonylation conditions for a sufficient period of time and under suitable pressure and temperature to form said acid derivative, with the proviso that said carbonylation conditions include conducting the reaction in a two-phase system wherein one phase is an aqueous medium which contains (1) a catalyst which is a water-soluble metal complex consisting essentially of a Group VIII metal and a hydrophilic ligand such as palladium complexed with trisulfonated triphenylphosphine, and (2) optionally an acid, and wherein the second phase comprises said arylcarbinol.

31 Claims, No Drawings

PROCESS FOR PREPARING ARYLACETIC ACID AND ARYLPROPIONIC ACID DERIVATIVES

BACKGROUND OF THE INVENTION

1. Field of the Invention

The present invention is directed to novel processes for the carbonylation of various substituted and unsubstituted arylcarbinols to selectively produce a wide variety of arylacetic acid and arylpropionic acid derivatives such as ibuprofen, flurbiprofen, ketoprofen, perprofen, fenoprofen, and naproxen. These carbonylations are carried out using, as a catalyst, a water-soluble metal complex consisting of a Group VIII metal and a hydrophilic ligand, for example, a palladium trisulfonated triphenylphosphine complex referred to herein as $Pd(TPPTS)_3$.

Arylacetic acids and their derivatives are valuable intermediate products for the production of drugs, scents, and aromatic substances.

2. Description of the Prior Art

The following prior art references are disclosed in accordance with the terms of 37 CFR 1.56, 1.97, and 1.93.

Chemtech, 1987, p. 570 (E.G. Kuntz) and Proc. 9th Int. Congr. Catal., 1988, Vol. 1, p. 254 (ed. M. J. Phillips and Ternan), collectively disclose the application of $RhH(CO)(t\text{-ppts})_3$ complex in industry in catalytic, two-phase hydroformylation of propylene.

U.S. Pat. No. 4,981,995 discloses carbonylation of benzylic alcohols catalyzed by $Pd/Ph_3P$ complexes in organic solvents.

U.S. Pat. No. 5,057,618 discloses complex compounds containing sulfonated phenyl phosphanes which can be used as catalysts for hydrogenations.

Angew. Chem., Vol. 105, pgs. 1588–1609 describes various hydrophilic ligands.

All of the above cited prior art references and any other references mentioned herein are incorporated herein by reference in their entirety.

SUMMARY OF THE INVENTION

The present invention provides a novel, low-cost, efficient process for preparing an arylacetic acid derivative from an arylcarbinol which comprises the step of subjecting said arylcarbinol to suitable carbonylation conditions for a sufficient period of time and under suitable pressure and temperature to form said arylacetic acid, with the proviso that said carbonylation conditions include conducting the reaction in a two-phase system wherein one phase is an aqueous medium which substantially contains (1) a catalyst which is a water-soluble metal complex consisting of a Group VIII metal and a hydrophilic ligand, for example, palladium complexed with trisulfonated triphenylphosphine and (2) with or without an acid, and wherein the second phase comprises said arylcarbinol.

DETAILED DESCRIPTION OF THE INVENTION

In the preparation of various types of arylacetic acid derivatives such as ibuprofen, one of the problems associated with the present day processes is the use of a catalyst directly in an organic solvent to convert the 1-(4'-isobutylphenyl) ethanol (IBPE) via carbonylation to ibuprofen, i.e. 2-(4'-isobutylphenyl) propionic acid. This requires, after reaction, separation of the desired end product (i.e. ibuprofen) from the catalyst in the overall reaction mass and recycling of the catalyst. There are substantial losses in catalyst as well as decreased efficiencies such as difficulties in the separation of the catalyst and the end product. Another problem associated with such process is the requirement that a halide ion, such as chloride, be used to facilitate the overall reaction. In this case, use of HCl, for example, handling creates metallurgical problems in the equipment used and the use of expensive equipment. These disadvantages with the prior art processes are overcome with the novel processes of the present invention. Accordingly, there is provided a novel, low-cost, and efficient process for preparing an arylacetic acid derivative from an arylcarbinol which comprises the step of subjecting said arylcarbinol to suitable carbonylation conditions for a sufficient period of time and under suitable pressure and temperature to form said arylacetic acid, with the proviso that said carbonylation conditions include conducting the reaction in a two-phase system wherein one phase is an aqueous medium which substantially contains (1) a catalyst which is a water-soluble metal complex consisting of a Group VIII metal and a hydrophilic ligand, for example, palladium complexed with trisulfonated triphenylphosphine, and (2) with or without an acid, and wherein the second phase comprises said arylcarbinol.

The starting materials of the present invention process are substituted or unsubstituted arylcarbinols which have the formula:

$$R_1\text{-C }(R_2)(R_3)(OH) \qquad (I)$$

wherein $R_1$ is selected from the group consisting of halogen, OH, $(C_1\text{-}C_8)$-alkyl, poly-fluoro-$(C_1\text{-}C_8)$-alkyl, CN, $(C_1\text{-}C_8)$-alkoxy, $NO_2$, COO-$(C_1\text{-}C_8)$-alkyl, $CON[(C_1\text{-}C_8)$-alkyl]$_2$, $NH(C_1\text{-}C_8)$-alkyl, $N[(C_1\text{-}C_8)$-alkyl]$_2$, $NH_2$, $SO_2H$, $SO_2(C_1\text{-}C_8)$-alkyl, $SO_2NH_2$, O—CO—$(C_1\text{-}C_8)$-alkyl, $CH_2$-halogen, substituted or unsubstituted phenyl, naphthyl, anthracenyl, phenanthrenyl, and $R_2$ and $R_3$ are each independently selected from the group consisting of hydrogen, halogen, —C(O)—$(C_1\text{-}C_8)$ alkyl, —O—C(O)—$(C_1\text{-}C_8)$ alkyl, $(C_1\text{-}C_8)$ alkyl and phenyl which can also be substituted with hydroxy and amino groups.

The desired products produced by the novel processes of the present invention are arylacetic acid derivatives which have the formula:

$$R_1\text{-C }(R_2)(R_3)(COOR_4) \qquad (II)$$

wherein $R_1$, $R_2$, and $R_3$ have the same definition as set forth above in Formula I, and $R_4$ is selected from the group consisting of hydrogen, $(C_1\text{-}C_8)$ alkyl, phenyl, and -C$(R_1)(R_2)(R_3)$ wherein $R_1$, $R_2$, and $R_3$ have the same designations as set forth above.

The process has decided benefits for compounds wherein $R_1$ stands for:

(III)

wherein $R_5$–$R_9$ are each independently selected from the group consisting of hydrogen, halogen, $(C_1\text{-}C_8)$-alkyl, OH, CN, poly-fluoro-$(C_1\text{-}C_8$-alkyl, O$(C_1\text{-}C_8)$-alkyl, $NO_2$, COO-$(C_1\text{-}C_8)$-alkyl, $CH_2$-halogen, COO$[(C_1\text{-}C_8)$-alkyl]$_2$ or phenyl or $R_5$ and $R_6$, $R_6$ and $R_7$, $R_7$ and $R_8$, or $R_8$ and $R_9$ together form an aromatic ring.

Important in this connection are compounds wherein $R_5$ to $R_9$, independently of one another, designate hydrogen, $CF_3$, halogen, $(C_1-C_4)$-alkyl, $(C_1-C_4)$-alkoxy, and OH. Halogen, as used herein, includes, without limitation, F, Cl, Br, and I.

The desired products produced by the present invention process and which fall within Formula II above, include, without limitation, ibuprofen, naproxen, fenoprofen, indoprofen, ketoprofen, flurbiprofen, perprofen, suprofen, cicloprofen, minoxiprofen, carprofen, benoxaprofen, bisiprofenum, fluprofen, clidimac, tertiprofen, hexaprofen, mexoprofen, pranoprofen, and the like.

Carbonylation of the arylcarbinol to an arylacetic acid derivative is conducted under suitable carbonylation conditions in order to achieve the desired end products. The carbonylation conditions include suitable temperatures and pressures to effect such process. The carbonylation with carbon monoxide (or suitable material which provides carbon monoxide in or to the reaction medium, such as synthesis gas —CO/$H_2$, e.g. 1:1 mixture) takes place at a temperature of at least about 5° C., preferably from about 50° C. to about 250° C., more preferably from about 50° C. to about 120° C., and at a pressure of at least about one atmosphere, preferably from about one atmosphere to about 200 atmospheres (1 bar–200 bars).

The time required to carry out this carbonylation reaction will vary considerably depending upon the starting material and the temperature and pressure used. Such reactions can take place in one minute or less, or take as long as 24 hours or more. This time aspect is not critical.

The carbonylation is conducted in a two-phase reaction system in which in one phase, there is an aqueous medium which contains (1) a catalyst which is a water-soluble metal complex consisting of a Group VIII metal and a hydrophilic ligand, and (2) with or without an acid. The second phase comprises the arylcarbinol.

In conjunction with the catalyst, it has been proven advantageous if the water-soluble metal complexes are compounds whose central atom is a Group VIII metal, in particular palladium, rhodium, cobalt, ruthenium, nickel, iron, and preferably palladium, rhodium, and cobalt. The water-soluble metal complex preferably contains hydrophilic ligands, especially hydrophilic phosphanes and amines, preferably sulfonated mono- and bis-phosphanes. Suitable hydrophilic ligands are described e.g. in Angew. Chem. 105, 1588–1609. It has been found that phosphanes yield especially good results. These compounds are made hydrophilic by introducing sulfonic acid groups, by hydrophilic groups at their periphery, by quartemized aminoalkyl- and amino-aryl-substituents, by carboxylation, by hydroxy-alkyl- or poly-ether substituents, and by monoquarternization of bis-phosphanes. Important representatives of these groups are e.g. phosphino-benzoic acids, phosphino-alkanols, phosphino-alkylphosphonium salts, salts of 3,3',3"-phosphane-tri-yl-benzol-sulfonic acid (tppts), salts of 3-diphenyl-phosphino-benzol-sulfonic acid (tppms), 1,2-bis-[bis-(sulfonato-phenyl)-phosphino]-ethane, 2,4-bis-[bis-(sulfonato-phenyl)-phosphino]-pentane, 1,2-bis-[bis(sulfonate-phenyl)-phosphino-methyl]-cyclobutane, 3,4-dimethyl-2,5,6-tris-(sulfonate-phenyl)-phosphano-bornane-2,4-diene, diphenyl-phosphino-ethane-sulfonate, 2-diphenyl-phosphino-ethyl-tri-methyl-ammonium salt, 2,4-bis-[bis-(tri-methyl-amino-phenyl)-phosphino]-pentane, and 3-diphenyl-phosphine-propionic acid.

A compound (catalyst) of palladium and tri-phenyl-phosphane-tri-sulfonate-sodium (tppts), sometimes referred to as palladium trisulfonated triphenylphosphine complex, i.e. Pd(TPPTS)3, has proven especially advantageous. This catalyst can be prepared according to Example 26 of U.S. Pat. No. 5,057,618.

The catalyst is used in quantities from 0.001 to 5 mole-%, especially 0.05 to 1.0 mole. %, preferably 0.1 to 0.5 mole. %, relative to the aryl carbinol. However, any amount of catalyst can be employed as long as the reaction takes place, i.e., the catalyst complex may be present in any amount in order to produce the desired end result.

The catalyst can also be advantageously prepared in situ from a readily accessible metal salt, e.g. a metal halogenide, sulfate, nitrate, and the ligand. Mixtures of various ligands, e.g. of mono- and bis-phosphanes can also be used.

In many cases, it has been proven advantageous to use a one to 40-fold, especially two to 20-fold, preferably three to 10-fold molar excess of ligands per mole of metal.

In the first phase, the acid, optionally employed, is preferably one which supplies weakly or non-coordinating artions. Such acids include, without limitation, Bronsted and Lewis acids and includes acids such as phosphoric acid, trifluoroacetic acid, and p-toluenesulfonic acid, sulfufic acid, and hexafluorophosphofic acid.

The amount of acid to be optionally employed in the two-phase system is any amount which will maintain the system, i.e. the first phase, in an acidic mode, e.g. pH of 1–7. Generally, such amount will range from about 0.001 mole percent to about 2.0 mole percent based on the total weight of the arylcarbinol used.

The carbonylation reaction is performed preferably in an agitated system of two mutually immiscible solvents (aqueous/organic). Suitable organic solvents that may be used include, without limitation, aromatic and aliphatic hydrocarbons, especially toluene, xylene, petroleum ether, hexane, iso-hexane, heptane, methyl ethyl ketone, acetone, 2-pentanone, 3-pentanone, acetophenone, benzene; and acyclic ethers such as tetrahydrofuran and dioxane. The organic solvent suitably is chosen such that the resulting aryl-acetic acid derivative is readily soluble in it. The solvent may be present in a weight ratio of solvent to arylcarbinol of from about 0 to about 1000: 1, preferably from about 0 to about 10: 1.

Furthermore, the addition of amphiphilic reagents (such as phase transfer reagents and surfactants such as tetra-alkyl-ammonium salts) or nucleophilic reagents (such as iodides) can improve the yield and/or the selectivity of the carbonylation process. Examples include, without limitation, tetrabutyl ammonium iodide.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

Preparation of 2-(4'-isobutylphenyl)propionic acid (ibuprofen)

$PdCl_2$ (35.5 mg, 0.2 mmol) and the sodium salt of trisulfonated triphenylphosphine (TPPTS) [ 1.136 g, 2 mmol, P/Pd=10] are charged into a tube under argon. To the mixture is added 50 g of deairated distilled $H_2O$. After 25 minutes of stirring at room temperature, the $PdCl_2$ is completely dissolved and the mixture becomes bright yellow, indicating complexation of palladium (II) with TPPTS (pH of the solution=3.42). The catalyst solution, 1-(4-isobutyl-phenyl)ethanol (IBPE) [445.7 mg, 2.5 mmol, IBPE/Pd= 12.5], p-toluenesulfonic acid monohydrate (190.2 rag, 1 mmol, $H^+$/IBPE=0.4) and deairated distilled $H_2O$ (90.4 g, [Pd]=150 ppm in the aqueous solution) are charged into a 300 ml Hastelloy C autoclave under argon. After a number of pressurizing-depressurizing cycles with CO to remove the last air, the autoclave is pressured to 30 bar (final pressure at reaction temperature) and contents are heated to 90° C. for 20 hours with stirring. The autoclave is cooled to room temperature, CO vented, and the reaction mixture is removed. Alter extraction with diethylether, the organic layer is separated from the aqueous layer (pH=2.21) and is dried over magnesium sulfate. The organic fraction, alter concentration under reduced pressure, is analyzed by HPLC and contains IBPE, 2-(4-isobutyl-phenyl)propionic acid (ibuprofen), 3-(4-isobutylphenyl)propionic acid (3-IPPA) which is a linear isomer of ibuprofen and traces of 4-isobutylstyrene. Conversion (based on IBPE) is 49%. Selectivity of ibuprofen is 61.5%. Selectivity of 3-IPPA is 38.3%.

EXAMPLE 2

The procedure of Example 1 is repeated, except that the reaction temperature is 80° C. Analyses shows the following: Conversion (based on IBPE) is 36%. Selectivity of ibuprofen is 69.4%. Selectivity of 3-IPPA is 29.9%, and there are traces of 4-isobutylstyrene.

EXAMPLE 3

Preparation of 2-phenyl propionic acid 6.04 g (40 mmol) 1-phenyl ethyl alcohol are dissolved in 30 ml toluene and are mixed with an aqueous solution of 1.14 g (2 mmol) tppts (=tri-phenyl-phosphane-tri-sulfonate-sodium salt) and 45 mg (0.2 mmol) $Pd(OAc)_2$ in 18 ml water. The two-phase system is filled into a 200 ml Hastelloy autoclave. 10.0 ml (1 molar) of a $H_2SO_4$ solution is added. The mixture is then heated to 70° C. at a CO pressure of 20 atmospheres. After a reaction time of 20 hours, the autoclave is cooled, the toluenic phase is separated and is evaporated to dryness. 4.78 g of a white crystalline material are obtained, which contains the product 93% pure. Recrystallization from iso-hexane yields 2-phenyl propionic acid. The yield is 4.18 g (30.6 mmol, 78% of theoretical).

EXAMPLE 4

Carbonylation of 1-phenyl ethyl alcohol under synthesis gas conditions

The reaction is performed as in Example 3, but in place of the CO, a mixture of $CO/H_2$ (1:1) is used. The yield is 4.31 g (31.8 mmol, 79.5% of theoretical).

EXAMPLE 5

Carbonylation of 1-phenyl ethyl alcohol in a 2-liter autoclave 106.27 g (810 mmol) 1-phenyl ethyl alcohol and 0.355 g (2 mmol) $PdCl_2$ are dissolved in 400 ml toluene and are filled into the autoclave. 11.43 g (20 mmol) tppts dissolved in 350 ml water, as well as 200 ml (1 molar) of a $H_2SO_4$ solution are added. The autoclave is heated to 70° C. and is brought to a pressure of 15 atmospheres with CO. After six hours, the reaction is completed, as can be recognized by the end of the gas uptake. The autoclave is cooled to room temperature, is relieved of pressure, the organic phase is separated from the aqueous catalyst phase, and the organic solution is evaporated to dryness. 94.14 g of a white product (2-phenyl propionic acid) are obtained. Yield after recrystallization from iso-hexane is 87.58 g (642 mmol, 80.3% of theoretical).

EXAMPLE 6

Carbonylation of 4-fluoro-benzylic alcohol 11.5 g (81 mmol) of 4-fluoro-benzylic alcohol and 45 mg (0.2 mmol) $Pd(OAc)_2$ are dissolved in 50 ml toluene. 2.28 g (4 mmol) tppts, dissolved in 25 ml $H_2O$ are added. The two-phase mixture is added to a 250 ml three-neck flask and is flushed several times with carbon monoxide. After five hours reaction time (70° C.), gas uptake has stopped. The toluenic phase is separated and is evaporated to dryness. 11.53 g raw product are obtained. After recrystallization, yield is 10.8 g (65.3 mmol, 80.8% of theoretical) of the pure product (4-fluoro-phenyl acetic acid).

EXAMPLE 7

Carbonylation of 1-(2'-chloro-phenyl)ethyl alcohol

The reaction is performed in accordance with Example 3, with 1-(2'-chlorophenyl)ethyl alcohol. $PdCl_2$ is used instead of $Pd(OAc)_2$. Pure yield is 47.5 (27.8 mmol, 69.1% of theoretical) of 2-(2'-chloro-phenyl)propionic acid.

EXAMPLE 8

Preparation of 2-(4'-isobutylphenyl)propionic acid (ibuprofen)

$PdCl_2$ (35.5 mg, 0.2 mmol) and the sodium salt of trisulfonated triphenylphosphine (TPPTS) [1.136 g, 2 mmol, P/Pd=10] are charged into a tube under argon. To the mixture is added 50 g of deairated distilled $H_2O$. After 25 minutes of stirring at room temperature, the $PdCl_2$ is completely dissolved and the mixture becomes bright yellow, indicating complexation of palladium (II) with TPPTS (pH of the solution is 3.42). The catalyst solution, 1-(4-iso-butyl-phenyl)ethanol (IBPE) [445.7 mg, 2.5 mmol, IBPE/Pd=12.5], deairated distilled $H_2O$ (90.4 g, [Pd]=150 ppm in the aqueous solution), and 20.0 ml (1 molar) of a $H_2SO_4$ solution are charged into a 300 ml Hastelloy C autoclave under argon. After a number of pressurizing, depressurizing cycles with CO to remove the last air, the autoclave is pressured to 30 bar (final pressure at reaction temperature) and the contents are heated to 90° C. for 20 hours with stirring. The autoclave is cooled to room temperature, CO vented, and the reaction mixture is removed. After extraction with diethylether, the organic layer is separated from the aqueous layer (pH is 2.21 ) and is dried over magnesium sulfate. The organic fraction, after concentration under reduced pressure, is analyzed by HPLC and contains IBPE, 2-(4-isobutylphenyl)propionic acid (ibuprofen), 3-(4-isobutylphenyl)propionic acid (3-IPPA) which is a linear isomer of ibuprofen and traces of 4-isobutylstyrene. Conversion (based on IBPE) is 61%. Selectivity ofibuprofen is 74.6%. Selectivity of 3-IPPA is 24.1%.

EXAMPLE 9

Preparation of Ibuprofen 5.7 g (41 mmol) IBPE is dissolved in 40 ml o-xylene. Together with a solution of 1.14 g (2 mmol) tppts and 3 mg (0.2 mmol) $PdCl_2$ in 20 ml $H_2O$, they are placed in a 250 ml three-neck flask. 15 ml (1 molar) of a $H_2SO_4$ solution is then added. The reaction mixture is agitated for 16 hours at T=70° C. under a CO atmosphere (standard pressure). At the end of the reaction time, the organic phase is separated and is evaporated to dryness. Yield is 4.44 g (71.5% of theoretical)

of ibuprofen. The palladium content in the product is determined by atomic absorption spectroscopy (AAS). It amounts to less than 1 ppm palladium and which indicates that there is little carry-over of the catalyst from the aqueous phase to the organic phase which contains the end product.

EXAMPLE 10

Comparison example of the prior art 5.7 g (41 mmol) IBPE, together with 0.54 g (2 mmol) tri-phenyl-phosphane and 35 mg (0.2 mmol) $PdCl_2$ are dissolved in 40 ml o-xylene. 10 ml (1 molar) of a $H_2SO_4$ solution and 20 ml $H_2O$ are added. The reaction mixture is then agitated for 16 hours at T=70° C. under a CO atmosphere (standard pressure). At the end of the reaction time, the aqueous phase is separated. The organic phase is evaporated to dryness. Yield is 1.05 g (17.0% of theoretical) of ibuprofen. The palladium content in the product is determined by AAS. It amounts to 110 ppm palladium which indicates that the water-insoluble catalyst in the organic phase is contaminating the final product.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing an arylacetic acid or arylpropionic acid derivative having the formula:

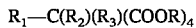

wherein $R_1$ is selected from the group consisting of:
1. phenyl
2. naphthyl
3. anthracenyl
4. phenanthrenyl, and
5. items 1–4 substituted with
   a. halogen
   b. OH
   c. ($C_1$–$C_8$) alkyl
   d. polyfluoro-($C_1$–$C_8$) alkyl
   e. CN
   f. ($C_1$–$C_8$) alkoxy
   g. $NO_2$
   h. COO-($C_1$–$C_8$) alkyl
   i. $CON_2$
   j. NH($C_1$–$C_8$) alkyl
   k. $N_2$
   l. $NH_2$
   m. $SO_2H$
   n. $SO_2$($C_1$–$C_8$) alkyl
   o. $SO_2NH_2$
   p. —O—CO—($C_1$–$C_8$) alkyl
   q. $CH_2$-halogen; and $R_2$ and $R_3$ are each independently selected from the group consisting of:
1. hydrogen
2. halogen
3. —C(O)—($C_1$–$C_8$) alkyl
4. —O—C(O)—($C_1$–$C_8$) alkyl
5. ($C_1$–$C_8$) alkyl
6. phenyl, and
7. phenyl which can be substituted with hydroxy and amino groups; and $R_4$ is selected from the group consisting of:
1. hydrogen
2. ($C_1$–$C_8$) alkyl
3. phenyl, and
4. —C($R_1$)($R_2$)($R_3$) wherein $R_1$, $R_2$, and $R_3$ have the same designations as set forth above, which comprises the step of reacting an arylcarbinol having the formula:

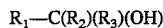

wherein $R_1$, $R_2$, and $R_3$ are the same as defined above, with carbon monoxide or synthesis gas, under carbonylation conditions, at a temperature of at least about 5° C. and at a pressure of at least about one atmosphere to form said acid derivative, with the proviso that said carbonylation conditions include conducting a reaction in a two-phase system wherein one phase is an aqueous medium which contains a catalyst which is a water-soluble metal complex consisting essentially of a Group VIII metal and a hydrophilic ligand and wherein the second phase comprises said arylcarbinol.

2. The process as set forth in claim 1 wherein said second phase additionally contains a hydrophobic organic solvent.

3. The process as set forth in claim 1 wherein said temperature is from about 50° C. to about 250° C.

4. The process as set forth in claim 1 wherein said pressure is from about one atmosphere to about 200 atmospheres.

5. The process as set forth in claim 1 wherein in said two-phase system there is also included an amphiphilic reagent.

6. The process as set forth in claim 1 wherein said first phase also contains an acid which is selected from the group consisting of phosphoric acid, trifluoroacetic acid, p-toluenesulfonic acid, sulfuric acid, and hexafluorophosphoric acid.

7. The process as set forth in claim 1 wherein said first phase also contains an acid which is an acid of weakly or non-coordinating anions.

8. The process as set forth in claim 1 wherein said first phase also contains an acid which is an acid of strongly coordinating anions.

9. The process as set forth in claim 1 wherein said acid derivative is ibuprofen.

10. The process as set forth in claim 1 wherein said acid derivative is naproxen.

11. The process as set forth in claim 1 wherein said acid derivative is an arylacetic acid derivative.

12. The process as set forth in claim 1 wherein said acid derivative is an arylpropionic acid derivative.

13. The process as set forth in claim 1 wherein the Group VIII metal is selected from the group consisting of palladium, rhodium, ruthenium, cobalt, nickel, and iron.

14. The process as set forth in claim 1 wherein the hydrophilic ligands are selected from the group consisting of hydrophilic phosphanes and hydrophilic amines.

15. The process as set forth in claim 1 wherein said ligand is selected from the group consisting of phosphino-benzoic acids, phosphino-alkanols, phosphino-alkyl-phosphonium salts, salts of 3,3',3"-phosphane-tri-yl-benzol-sulfonic acid (tppts), salts of 3-diphenyl-phosphino-benzol-sulfonic acid (tppms), 1,2-bis-ethane, 2,4-bis-pentane, 1,2-bis-cyclobutane, 3,4-dimethyl-2,5,6-tris-(sulfonate-phenyl)-phosphino-borna-2,4-diene, diphenyl-phosphino-ethane-sulfonate, 2-diphenyl-phosphino-ethyl-tri-methyl-ammonium salt, 2,4-bis-pentane, 3-diphenyl-phosphine-propionic acid.

16. The process as set forth in claim 1 wherein said catalysts comprises a compound of palladium and tri-phenyl-phosphane-tri-sulfonate-sodium (tppts).

17. The process as set forth in claim 1 wherein the catalyst is used in quantities from about 0.001 to about five mole percent, relative to the arylcarbinol.

18. The process as set forth in claim 1 wherein the water-soluble metal complex is produced in-situ from a metal salt and the ligand.

19. The process as set forth in claim 18 wherein the catalyst is produced in-situ with a one to forty-fold molar excess of ligands.

20. The process as set forth in claim 1 wherein halogen is selected from the group consisting of Cl, Br, I, and F.

21. The process as set forth in claim 1 wherein the carbonylation is performed at a temperature of from about 50° C. to about 120° C.

22. The process as set forth in claim 1 wherein the two-phase system includes water or an alcohol/water mixture and an aromatic or aliphatic hydrocarbon.

23. The process as set forth in claim 1 wherein $R_1$ has the general formula:

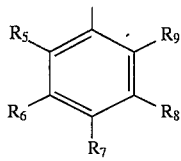

wherein $R_5$–$R_9$ are each independently selected from the group consisting of hydrogen, halogen, $(C_1$–$C_8)$-alkyl, OH, CN, poly-fluoro-$(C_1$–$C_8)$-alkyl, $O(C_1$–$C_8)$-alkyl, $NO_2$, COO-$(C_1$–$C_8)$-alkyl, $CH_2$-halogen, COO-$(C_1$–$C_8)$-alkyl, phenyl, and $R_5$ and $R_6$, $R_6$ and $R_7$, $R_7$ and $R_8$, or $R_8$ and $R_9$ together form an aromatic ring.

24. The process as set forth in claim 23 wherein $R_5$ to $R_9$ are independently selected from the group consisting of hydrogen, $CF_3$, halogen, $(C_1$–$C_4)$-alkyl, $(C_1$–$C_4)$-alkoxy, and OH; and halogen is selected from the group consisting of F, Cl, Br, and I.

25. A process for preparing 2-(4'-isobutylphenyl) propionic acid which comprises the step of reacting 1-(4'-isobutylphenyl)ethanol with carbon monoxide or synthesis gas in a two-phase carbonylation reaction system at a temperature of at least about 5° C. and at a pressure of at least about one atmosphere to form said propionic acid, with the proviso that one phase is an aqueous medium which substantially contains (1) a catalyst which is a water-soluble metal complex consisting essentially of a Group VIII metal and a hydrophilic ligand, and (2) an acid; and the second phase comprises said ethanol.

26. The process as set forth in claim 25 wherein said second phase additionally contains a hydrophobic organic solvent.

27. The process as set forth in claim 25 wherein said temperature is from about 50° C. to about 250° C.

28. The process as set forth in claim 25 wherein said pressure is from about one atmosphere to about 200 atmospheres.

29. The process as set forth in claim 25 wherein in said two-phase system, there is also included an amphiphilic reagent.

30. The process as set forth in claim 25 wherein said catalyst is palladium complexed with trisulfonated triphenylphosphine (tppts).

31. The process as set forth in claim 25 wherein the hydrophilic ligands are selected from the group consisting of hydrophilic phosphanes and hydrophilic amines.

* * * * *